March 2, 1971 F. K. ISHIDA Plant Pat. 3,030

AZALEA PLANT

Filed April 21, 1969

INVENTOR.

FRANK K. ISHIDA,

By Edmond F. Shanahan.

ATTORNEY.

United States Patent Office

Plant Pat. 3,030
Patented Mar. 2, 1971

3,030

AZALEA PLANT

Frank K. Ishida, South Gate, Calif., assignor to Monrovia Nursery Company, Azusa, Calif.

Filed Apr. 21, 1969, Ser. No. 818,160
Int. Cl. A01h *5/00*
U.S. Cl. Plt.—57 1 Claim

Figure 2:
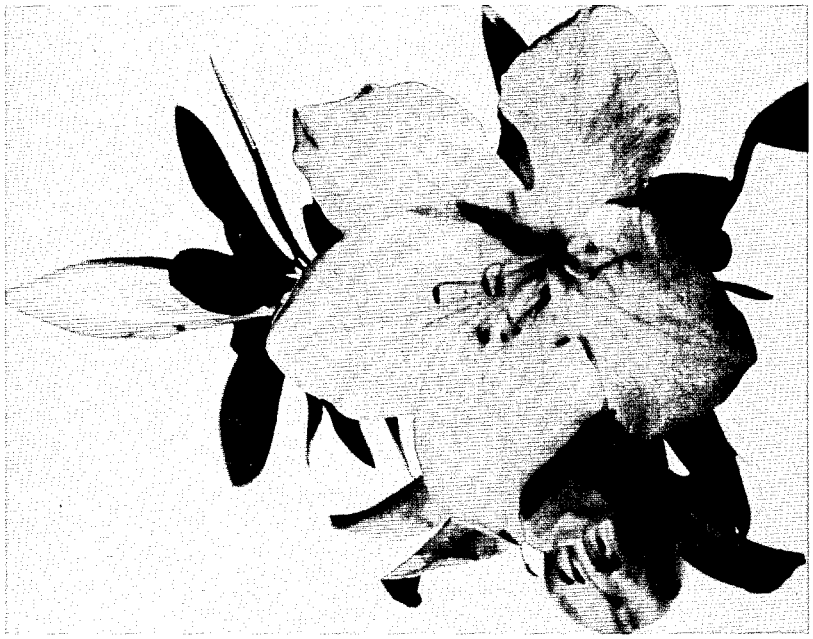

The present discovery relates to a new and distinct variety of the Rhododendron genus, Azalea species characterized as to novelty by its large brilliantly colored flowers, its vigorous compact habit of growth, and its dark green foliage.

The new variety was discovered by me growing as a chance seeedling in a bed of azalea seedlings being grown by me, at my nursery in southern California from some seed collected by my father in Japan. Neither the pollen parent nor the seed parent of this plant is known. The plant was selected by me when it first flowered in 1954, because of its large brilliantly colored flowers (mostly a kind of cardinal red). The plant has been asexually propagated by me and all descendants have shown the same characteristics which show that the descendants are true and that the new variety has become well established. It does not reproduce true from seed.

A flower and plant of the new variety are shown in full color in the accompanying illustration.

A detailed description of the new variety follows, and to facilitate identification of the important colors the color terminology adopted by the British Horticultural Color Charts has been followed.

THE PLANT

Parentage: Chance seedling resulting from open pollination.

*Seed parent*—Unknown.

*Pollen parent.*—Unknown.

Growth: The plant is of moderately vigorous upright habit of growth with a dense branching habit. Well clothed with foliage. The ultimate height of the plant is not known, but under normal condition should reach a height of from 5 to 6 feet with a spread of from 6 to 7 feet being only slightly wider than tall.

Branches: New growth has a reddish tinge gradually changing to a light green and then to a light brown at maturity. The new growth is densely hairy which disappears as the branch matures.

Growth habit: Branching starts from just above ground level and has a tendency to be arching.

Foliage: The leaves are of good substance and are a dull green in color.

Shape: The leaves are best described as being elliptic to oblanceolate. Margins are entire and ciliate. Apex is mucronulate, base is attenuate.

Size: Leaves are from 1¾ to 2¾ inches in length and from ½ to 1 inch in width. Petiole is from ⅛ to 3/16 inches in length.

Arrangement: Leaves are alternate on the branches.

Veins: Midrib on the upperside is recessed and strigose hairy, lighter in color than the blade. Midrib underneath is prominent and strigose hairy.

Color: New leaves are semi-glossy 0960 Spinach Green above, and 860 Scheeles Green beneath. Mature leaves are dull 00962 Parsley Green above, and 0960/1 Spinach Green beneath. On both new leaves and mature leaves both surfaces are remotely strigose hairy.

THE FLOWER

The plant sets an occasional bloom from late September until late January or early February, reaching its peak of bloom in March, after which it will produce an occasional bloom until early May.

Form: Flowers are single with a natural spread of from 3¼ to 3¾ inches, with a depth of 2½ inches.

Petals: Petals are five in number, standard petal 1⅝ inches, upper and lower wing petals 1¾ inches, tube 1 inch.

Stamens: Usually 7, sometimes 8, they vary in length from 1⅞ to 2⅜ inches. Filaments light pink, anthers maroon.

Pistil: Pistil is 2⅝ inches long, style Cardinal red in color.

Color: Flower is of one color 020/1 Delft Rose. The standard petal and the two upper wing petals are blotched with 822 Cardinal Red.

Figure 1:
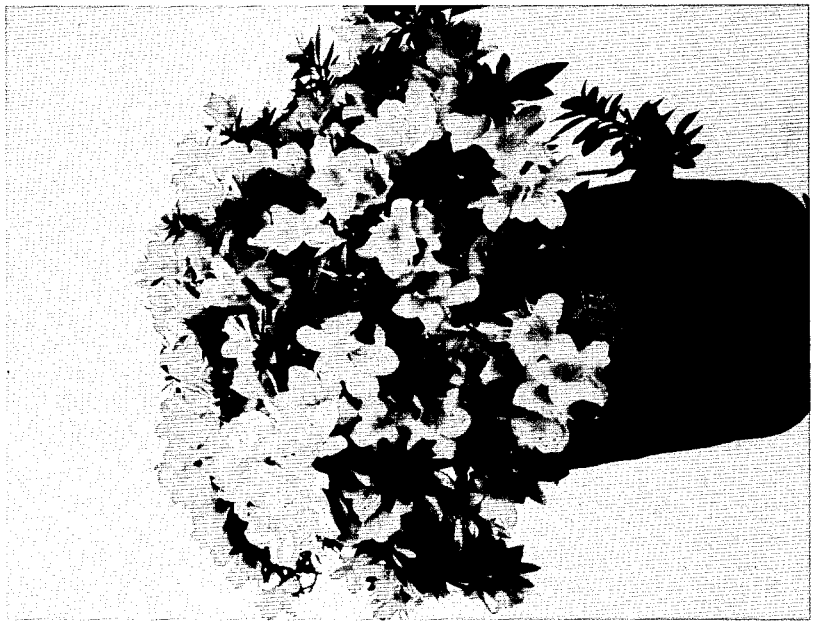

FIG. 1 shows the true blossom color, while FIG. 2 is presented only to illustrate the blossom structure in detail.

I claim:

1. A new and distinct variety of azalea plant, substantially as described and illustrated herein, and characterized by the large size and unique, brilliant color of its flowers, dense branching, and dark green foliage.

No references cited.

ROBERT E. BAGWILL, Primary Examiner